United States Patent
Yoon

(10) Patent No.: US 9,649,440 B2
(45) Date of Patent: May 16, 2017

(54) SYRINGE DEVICE FOR SKIN TREATMENT

(71) Applicant: PANACE CO., LTD., Gyeonggi-do (KR)

(72) Inventor: Sung Tae Yoon, Seoul (KR)

(73) Assignee: PANACE CO., LTD., Seongnam-si, Gyeonggi-Do (KR)

( * ) Notice: Subject to any disclaimer, the term of this patent is extended or adjusted under 35 U.S.C. 154(b) by 698 days.

(21) Appl. No.: 14/103,181

(22) Filed: Dec. 11, 2013

(65) Prior Publication Data

US 2015/0157802 A1 Jun. 11, 2015

(51) Int. Cl.
*A61M 5/00* (2006.01)
*A61M 5/20* (2006.01)
*A61M 5/46* (2006.01)
*A61M 5/315* (2006.01)

(52) U.S. Cl.
CPC ............... *A61M 5/20* (2013.01); *A61M 5/46* (2013.01); *A61M 2005/2013* (2013.01); *A61M 2005/31588* (2013.01)

(58) Field of Classification Search
CPC ........... A61M 2005/2013; A61M 2005/31588; A61M 5/20; A61M 5/31535; A61M 5/46
USPC ....................................................... 604/188
See application file for complete search history.

(56) References Cited

U.S. PATENT DOCUMENTS 4,544,369 A * 10/1985 Skakoon ............. A61M 5/1456
128/DIG. 12

FOREIGN PATENT DOCUMENTS

| KR | WO 2012057424 A1 * | 5/2012 | .......... A61M 5/1452 |
| KR | EP 2633873 A1 * | 9/2013 | .......... A61M 5/1452 |

* cited by examiner

*Primary Examiner* — Jason Flick
(74) *Attorney, Agent, or Firm* — Rabin & Berdo, P.C.

(57) ABSTRACT

A syringe device for skin treatment is provided, which includes a syringe for injecting a drug into a skin through a needled at an end, a syringe seat connected with a cylinder of the syringe receiving the drug therein to allow a reciprocation of the cylinder within a limited range according to a direction of injecting the drug, a mount formed on the syringe seat and to which the cylinder of the syringe is fixed, an injector mounted on one side of the syringe seat to be rotated by a driving force to move in association with movement of the syringe seat to move a rod of the cylinder toward a needle, and a controller mounted on one sides of the syringe seat and the injector to operate the injector when the needle is in contact with the skin and the syringe seat is moved to one end within a limited range, and stop the injector when the needle is apart from the skin and the syringe seat is moved to opposite end within the limited range. Accordingly, waste of drug can be avoided, because the syringe seat to allow reciprocation of the syringe cylinder and the controller ensure that the rod of the cylinder for injecting drug is moved by an appropriate distance.

4 Claims, 5 Drawing Sheets

SYRINGE DEVICE FOR SKIN TREATMENT

BACKGROUND

1. Field of the Invention

The present invention relates to a syringe device for skin treatment, and more particularly, to a syringe device for skin treatment which allow rapid and efficient introduction of drug into a body, while ensuring that the drug is introduced through a skin to an accurate depth in an appropriate amount, without causing drug overuse or waste.

2. Description of the Related Art

A particular treatment (hereinbelow, 'multi-hole therapy') that pierces a plurality of fine cavities in skin and allows substance like drug to be introduced into a body therethrough is generally and widely practiced to remove a variety of skin troubles such as wrinkles, spots, blemishes, stretch marks, acne, freckles, or pigmentation, maintain hair condition, improve hair loss, treat obesity, and for other various purposes.

The multi-hole therapy can particularly provide fast treatment effect, because it utilizes skin tissues' regenerative power to induce generation of new skin from damaged one, or allows substance like drug to be introduced through fine holes.

While the drug for use in such multi-hole therapy can provide effect precisely and evenly over the entire skin when it is introduced by a small amount and into a plurality of administrations which are adapted for the specific purpose as intended, it is difficult for a practitioner to ensure that the drug is in a precise amount because he/she injects the drug mostly relying on feeling on his/her arm and finger muscles and feeling that the syringe is inserted into the skin. Therefore, the drug is sometimes injected in an amount more than necessary, in which case the drug leaks out, causing waste of the drug which is generally very pricey.

SUMMARY

Exemplary embodiments of the present inventive concept overcome the above disadvantages and other disadvantages not described above. Also, the present inventive concept is not required to overcome the disadvantages described above, and an exemplary embodiment of the present inventive concept may not overcome any of the problems described above.

The invention has been made to overcome the problems occurring in the related art, and accordingly, it is an object of the present invention to provide a syringe device for skin treatment which allows rapid and efficient introduction of a drug into a body, and to a precise depth suitable for a subject of treatment, without causing any pain of the subject of treatment, and with increased efficiency.

To achieve the objects mentioned above, a syringe device for skin treatment according to an embodiment is provided, which may include a syringe in which drug is injected into a skin through a needled at an end; a syringe seat engaged with the cylinder of the syringe receiving the drug therein to allow reciprocation of the cylinder within a limited range along a direction of injecting the drug; a mount formed on the syringe seat and to which the cylinder of the syringe is fixed; an injector mounted on one side of the syringe seat to be rotated by a driving force and move in association with the movement of the syringe seat to move the rod of the cylinder toward the needle; a push rod connected with the injector and contacted with the rod; and a controller configured to operate the injector when the needle is in contact with the skin, or stop the injector when the needle is apart from the skin, and move the push rod backward by a distance that the cylinder has to retreat toward the injector.

According to various embodiments, the structure includes the syringe seat to allow reciprocation of the syringe cylinder and the injector that moves toward the needle and moves the rod of the cylinder to inject the drug by an appropriate distance according to the controller. As a result, drug waste can be avoided.

Further, the controller operates or stops the injector by sensing a moved location of the syringe seat in accordance with presence/absence of the contact of the end of the needle with the skin and insertion of the needle. Accordingly, the drug can be injected in an accurate amount.

Furthermore, according to embodiments, a distance of reciprocal movement of the cylinder on the syringe seat is adjustable, and therefore, it is possible to accurately adjust the depth of the needle inserted in the skin for treatment.

BRIEF DESCRIPTION OF THE DRAWINGS

The above and/or other aspects of the present inventive concept will be more apparent by describing certain exemplary embodiments of the present inventive concept with reference to the accompanying drawings, in which.

DETAILED DESCRIPTION OF EXEMPLARY EMBODIMENTS

Figure 1:
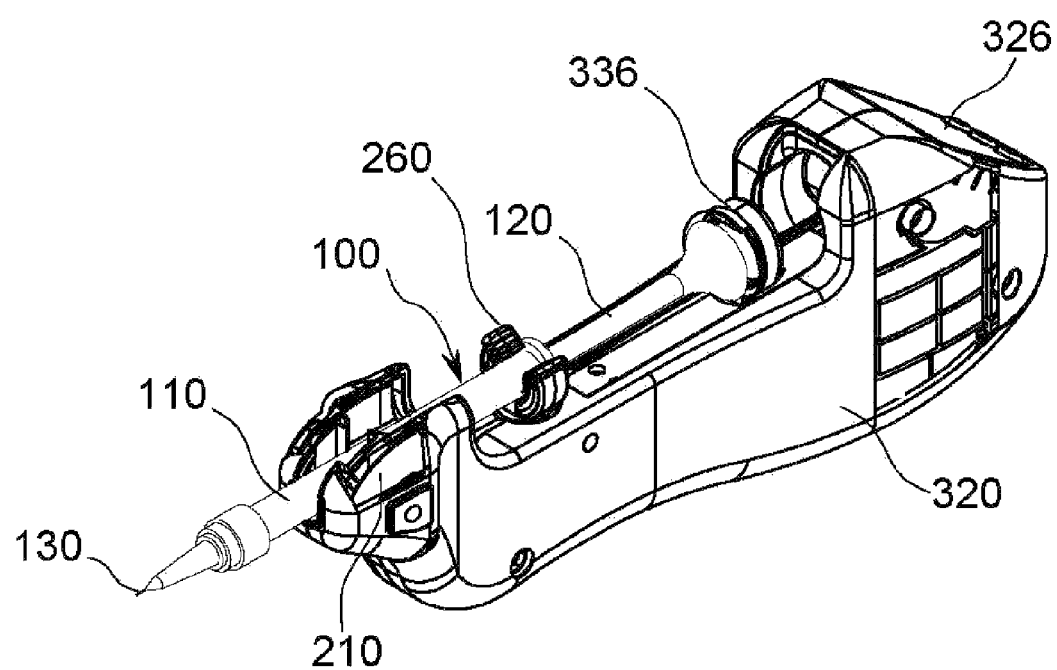
FIG. 1 is a perspective view of a syringe device for skin treatment according to an embodiment.

Certain exemplary embodiments of the present inventive concept will now be described in greater detail with reference to the accompanying drawings.

In the following description, same drawing reference numerals are used for the same elements even in different drawings. The matters defined in the description, such as detailed construction and elements, are provided to assist in a comprehensive understanding of the present inventive concept. Accordingly, it is apparent that the exemplary embodiments of the present inventive concept can be carried out without those specifically defined matters. Also, well-known functions or constructions are not described in detail since they would obscure the invention with unnecessary detail.

Figure 2:
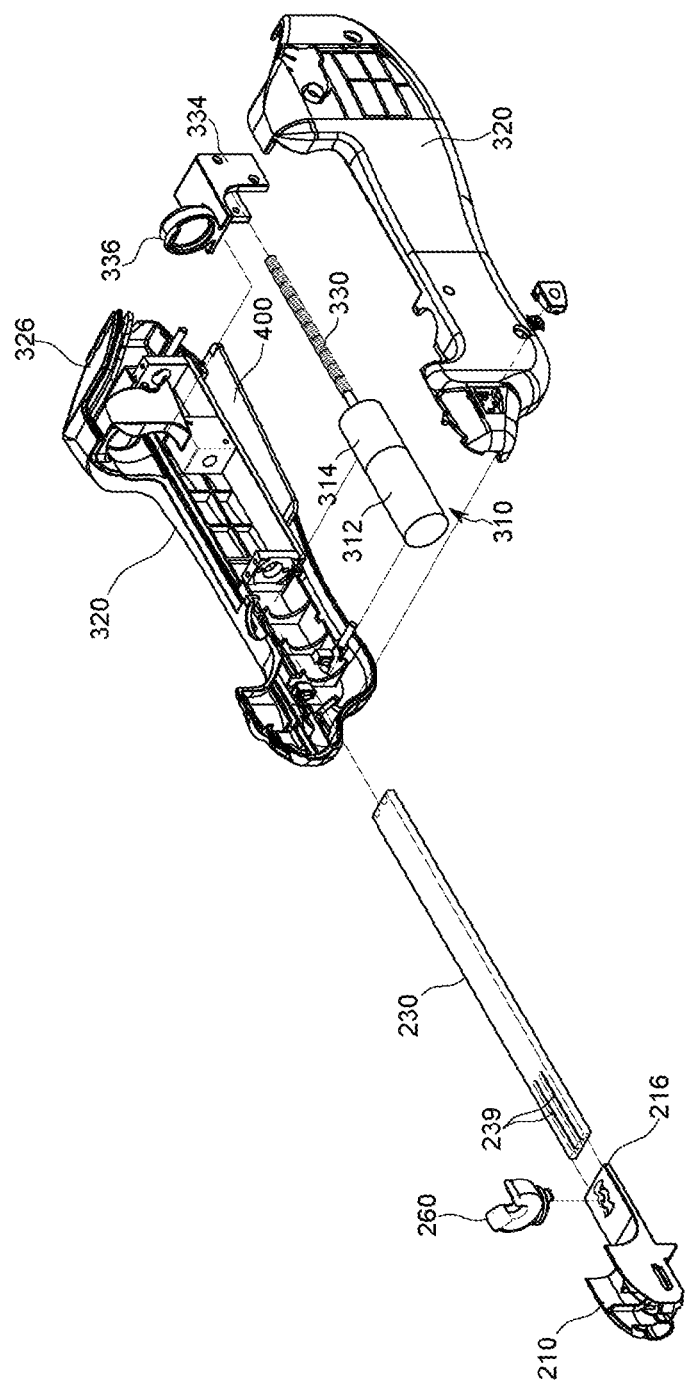
FIG. 2 is an exploded perspective view of a syringe device for skin treatment according to an embodiment.
Figure 3:
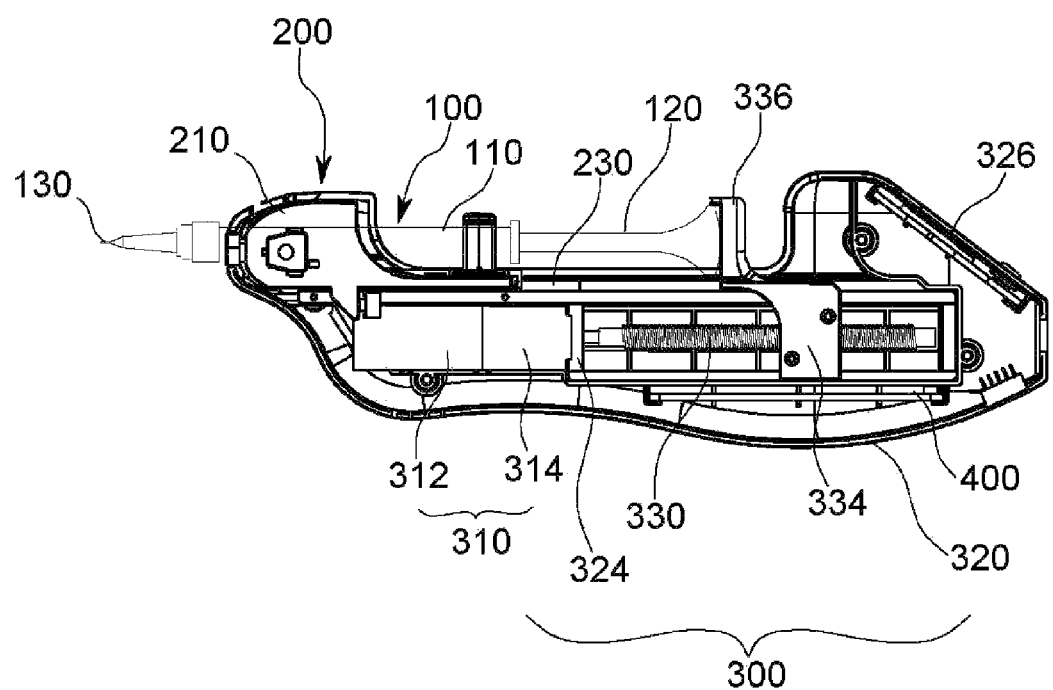
FIG. 3 is a cross-section view of a syringe device for skin treatment according to an embodiment.
Figure 4:
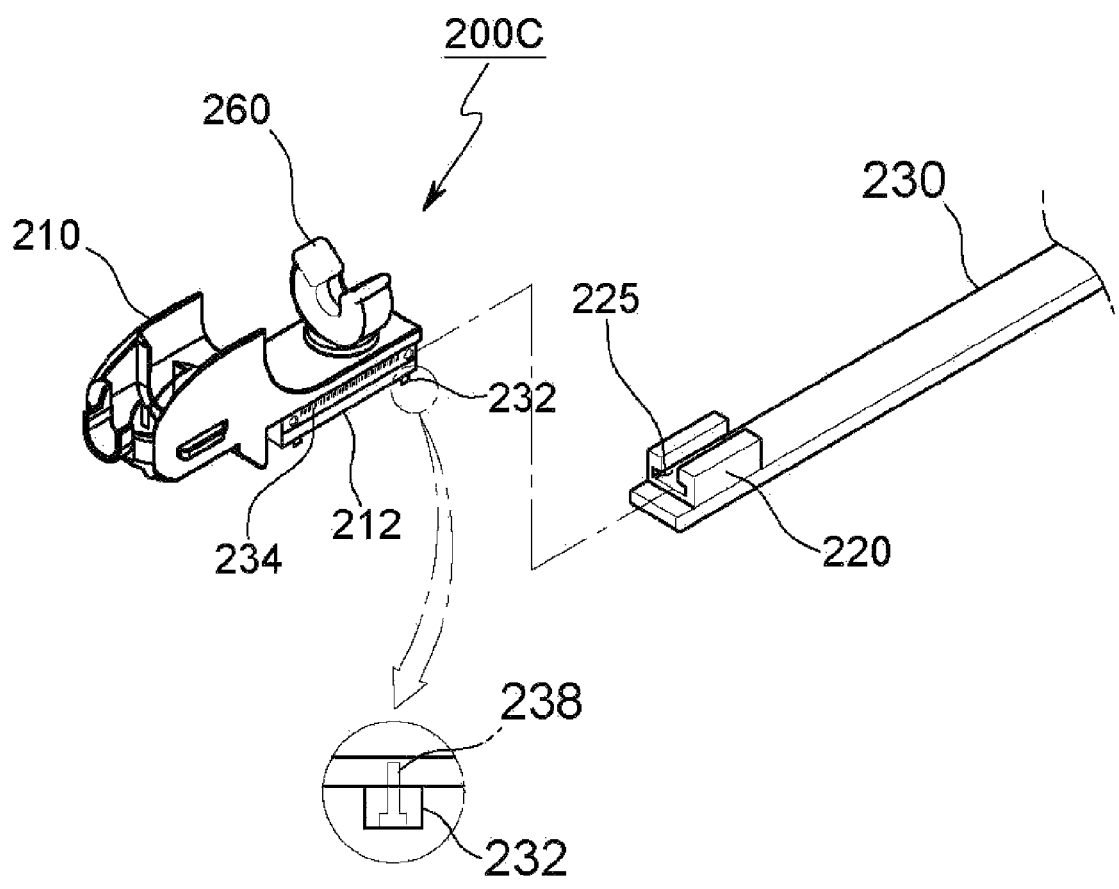
FIG. 4 is an exploded perspective view of a syringe seat of a syringe device for skin treatment, according to another embodiment.
Figure 5:
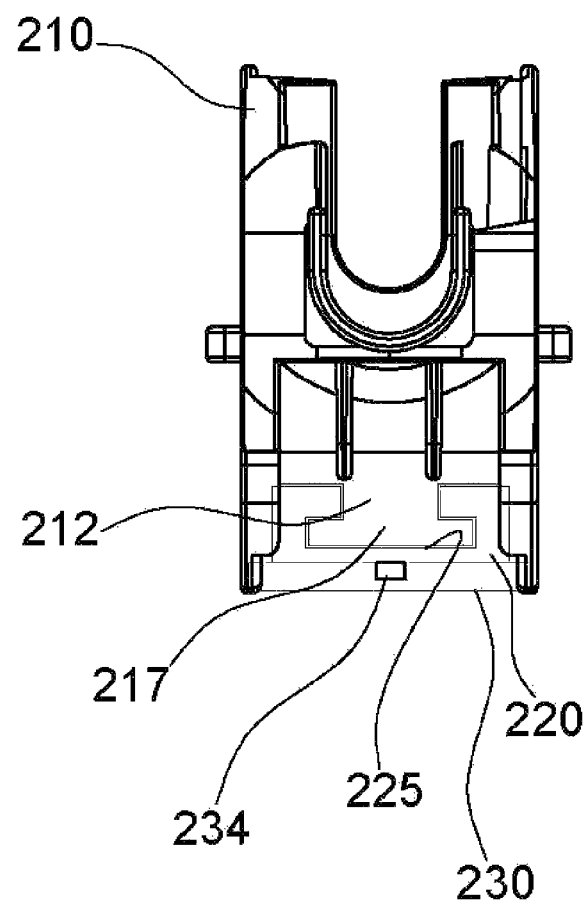
FIG. 5 is a front view illustrating assembled state of FIG. 4.

FIG. 1 is a perspective view of a syringe device for skin treatment according to an embodiment, FIG. 2 is an exploded perspective view of a syringe device for skin treatment according to an embodiment, FIG. 3 is a cross-section view of a syringe device for skin treatment according to an embodiment, FIG. 4 is an exploded perspective view of a syringe seat of a syringe device for skin treatment, according to another embodiment, and FIG. 5 is a front view illustrating assembled state of FIG. 4.

Referring to FIGS. 1 to 5, the syringe device for skin treatment according to an embodiment may include a syringe 100 which is connected to a syringe seat 200 in a reciprocally moveable manner, an injector 300 configured to inject a predetermined amount of drug, and a controller 400 configured to operate and stop the injector 300.

The syringe 100 thus injects drug into skin through a needle 130 mounted to an end of a cylinder 110 holding the drug therein, while a rod 120 moves towards the needle 130.

The syringe seat 200 may include a mount 210 on which the cylinder 110 of the syringe 100 holding drug therein is fixed, and a guide rail 230 of which a front portion is connected to the mount.

The syringe seat 200 may take a variety of forms which may mainly include the following three forms.

According to a first embodiment, the syringe seat 200 may include a mount 210 and a holder 260 to which the cylinder 110 of the drug-holding syringe 100 is fixed, and a guide rail 230 of which a front portion is connected to the mount 120, in which the mount 210 may be integrally fixed to a front end of the guide rail 230.

Meanwhile, according to a second embodiment, the syringe seat 200 may include a mount 210 to which the cylinder 110 of the drug-holding syringe 100 is fixed, and a guide rail 230 of which a front portion is connected to the mount, in which the mount 210 may include an insert hole 216 to fittingly receive therein the front end of the guide rail 230, and the guide rail 230 may include a guide groove 239 of a predetermined length formed on a front portion thereof.

Accordingly, because the mount 210 is so configured to move to and pro by the length of the guide groove 239, when the needle 130 deviates from the skin in a state that the drug in the cylinder 110 is under increased pressure due to rod 120 compression, the cylinder 110 can slightly advance by the inertia and due to the pressure of the drug in the cylinder 110, thus relieving the over-pressure inside the cylinder 110 and subsequently preventing drug leakage.

According to a third embodiment, the syringe seat 200C may include a mount 210 to which the cylinder 110 of the drug-holding syringe 100 is fixed, a sub-rail 212 formed under the mount 210, and a support block 220 which is formed on a front portion of the guide rail 230 and connected to the sub-rail 212.

The syringe seat 200C may be fixedly gripping the cylinder 110 while the rod 120 of the syringe 100 is moved forward or backward by the injector 300.

In response to a signal from the controller, the syringe seat 200 including the syringe 100 reciprocates forward and backward within a predetermined region of the sub-rail 212, thus contact of the needle 130 to the skin is controlled to be within a predetermined distance with respect to the skin.

That is, a graduated ruler 236 may be attached by a screw to an edge of the sub-rail 212, to enable one to observe with eyes and accurately adjust a moving distance, i.e., adjust a depth for the needle 130 to be inserted in the skin.

The support block 220 is formed on a front upper surface of the guide rail 230.

The sub-rail 212 is formed on a lower surface of the mount 210, and as the rail protrusion 217 formed on a lower surface of the sub-rail 212 is engaged with the rail groove 225 of the support block 220, the mount 210 is reciprocatingly moveable along the sub-rail 212.

The sub-rail 212 may include stoppers 232, 234 which may be formed on a front end and a rear end, respectively.

The stoppers 232, 234 may limit a reciprocating distance of the mount 210 according to movement of the sub-rail 212 engaged with the support block 220.

The support block 220 and the sub-rail 212 may be so engaged with each other as to enable precise and fine adjustment of the moving distance, by the graduated ruler 236 which may be provided on an edge of the sub-rail 212 and which enables one to observe with eyes and precisely adjust the moving distance, i.e., a depth for the needle 130 to be inserted in the skin.

Accordingly, distance (d) between the support block 220 in contact with a first stopper 232 of the stoppers 232 on the front and rear ends 232, 234 and a second stopper 234 opposite to the first stopper 232, is equal to the depth for the needle 130 to be inserted into the skin.

The sub-rail 212 may include an adjustment screw 238 to fix the first stopper 232 of the stoppers 232, 234 on the front and rear ends, which is reciprocatingly mounted on the guide rail 220.

Accordingly, a practitioner may loosen the adjustment screw 238 and move the first stopper 232 and adjust a depth fort the needle 130 to be inserted into the skin, to thus adjust the depth of drug injection into the skin to accurately suit the purpose of the treatment as applied.

Meanwhile, the injector 300 is so configured as to continue or stop movement of the rod 120 toward the needle 130 by the controller 400, in which a driving force member 310 transmits driving force, includes a driving motor 312 and a reducer 314 received in a casing 320, and transmits driving force to the rod 120 while being operated or stopped according to the controller 400.

The driving force member 310 is connected to a shaft 330, the shaft 330 is screw-coupled with a moving segment 334, and the moving segment 334 is engaged with a push rod 336 which is contacted to a rear end of the rod 120.

The casing 320 includes a space to receive the driving force member 310 therein, the guide rail 220 is mounted on the upper surface along a lengthwise direction of the casing 320, the support block 220 is connected to a leading end of the guide rail 220, a supporting segment 324 is formed so that the driving force member 310 is fixedly mounted thereon, and a display window 326 is formed on a rear portion.

The shaft 330 is connected to the driving force member 310, i.e., to the reducer 314 and the rod 120, respectively, to be moved in association with the driving force member 310 to convert a rotary motion into a reciprocal motion along lengthwise direction of the casing 320, thus moving the rod 120 toward the needle 130. The moving segment 334 is screw-coupled, and the push rod 336 for close-contact with the rod 120 is integrally formed on the moving segment 334.

The driving motor 312 of the driving force member 310 is received in the casing 320 and rotated forward and backward, and the reducer 314 is mounted between the driving motor 312 and the shaft 330 to reduce the rotational speed of the driving motor 312 to a speed suitable to slowly move the rod 120 toward the needle 130.

One end of the shaft 330 is connected to an end of the driving force member 310 to be rotated forward and backward, with the other end being supported on the casing 320. A screw thread is formed along an outer circumference.

The moving segment 334 is screw-coupled with the shaft 332 to be reciprocated along the lengthwise direction of the shaft 332. The push rod 336 is formed on an upper portion.

The push rod 336 is engaged with the moving segment 334, contacted with the rod 120 and moved along the guide rail 220 of the casing 320, while being exposed through an upper portion of the casing, thus causing the rod 120 to move toward the needle 130.

Meanwhile, the injector 300 is formed under the syringe seat 200 and rotated by the driving force of the motor 312, thus causing the rod 120 of the cylinder 110 to be moved toward the needle 130 in association with the movement of the syringe seat 200.

The controller 400 is mounted on one sides of the syringe seat 200 and the injector 300, and includes a PCB embedded with a microcomputer to calculate depth for needle insertion into skin and dose of drug injection.

According to the controller 400 as programmed, when the end of the needle 130 is in contact with the skin and pressed against the same, the injector 300 is operated when the syringe seat 200 is moved to one end within a limited range.

When the end of the needle 130 is distanced away from the skin, so that the syringe seat 200 is moved to the other end within the limited range, the injector 300 is stopped, and an appropriate amount of drug is injected into the skin through the needle 130.

That is, the injector 300 enables injection of an accurate amount of drug, by moving the rod 120 toward the needle 130 by a distance that the cylinder 110 retreats toward the injector 300.

Meanwhile, the controller 400 may include a sensing means (not illustrated) to control the operation of the injector 300.

Using the sensing means, when the end of the needle 130 is inserted in contact with the skin, the controller 420 may control the injector 300, i.e., the driving motor 312 of the driving force member 310 to rotate or stop, depending on whether the support block 220 is moved to one end of the guide rail 230 or to the opposite end of the guide rail 230.

The sensing means may be mounted on the syringe seat 200, i.e., on a leading end of the guide rail 220 to transmit a detect signal to the controller 400, thus indicating that the leading end (left-hand side of the drawing) of the guide rail 230 is in contact with the support block 220 when the guide rail 220 is mounted on the leading end and the needle 130 is contacted to and inserted into the skin.

The sensing means may be mounted on the leading end of the guide rail 220, but not limited thereto. Accordingly, a spring-embedded switch mounted on a rear end of the guide rail 220, such as, for example, limit switch, position detecting sensor or pressure detecting sensor may be used.

An example of the sensing means may be a spring-embedded switch mounted on a rear end of the guide rail 220. Accordingly, a signal transmission system for operating the injector 300 is completed, in which the overall circuit is connected or disconnected according to the force detected, when the guide rail 220 is moved and contacted with the support block 220.

When a detect signal is transmitted from the sensing means, the controller transmits an electric signal to operate or stop the driving motor 312.

Hereinbelow, an example of treatment with a skin treatment syringe device according to an embodiment will be explained.

According to a first embodiment, the driving motor 312 is driven to rotate the shaft 330, and accordingly, to move the moving segment 334 screw-coupled thereto forward or backward, thus moving the push rod 336 subordinate to the moving segment 334 forward or backward.

Accordingly, as the push rod 336 pushes the rod 120 in a forward direction, the drug in the cylinder 110 is released through the needle 130 and injected into the skin.

As a result, with the needle 130 inserted in the skin, the injector 300 is continuously operated so that the drug of the cylinder 110 is injected through the needle 130.

When an appropriate amount of drug is injected, the needle 130 is distanced away from the skin, and the driving motor 312 is rotated backward, in association with which the push rod 336 is retreated away from the rod 120.

The sensing means senses that the needle 130 is distanced apart from the skin, and almost simultaneously, the driving motor 312 starts rotating backward.

Accordingly, due to the pressure formed within the cylinder 110 after distancing from the rod 120, piston and rod 120 are gravitated backward, thus relieving the internal pressure and ensuring that drug loss does not occur.

According to a second embodiment, the driving motor 312 is operated, the shaft 330 is rotated, and accordingly, the moving segment 334 and the push rod 336 are moved forward.

As a result, as the push rod 336 pushes the rod 120 forward, the drug within the cylinder 110 is released through the needle 130 and injected into the skin.

Accordingly, with the needle inserted in the skin, the injector 300 is continuously operated to continuously inject the drug within the cylinder 110 through the needle 130.

When an appropriate amount of drug is injected, the needle 130 is distanced apart from the skin and the operation of the injector 300 is discontinued.

As the driving motor 312 stops, the force that presses on rod 120 is ceased, and therefore, the pressure formed in the cylinder 110 causes the cylinder 110 and the syringe seat to gravitate forward along the guiding groove 239, thus relieving the internal pressure. Therefore, drug loss can be avoided.

According to a third embodiment, the driving motor 312 is driven, the shaft 330 is rotated, and accordingly, the moving segment 334 and the push rod 336 are moved forward.

As the push rod 336 pushes the rod 1020 forward, the drug within the cylinder 110 is released through the needle 130 and injected into the skin.

Accordingly, with the needle 130 inserted in the skin, the injector 300 is continuously operated to inject the drug within the cylinder 110 through the needle 130.

When an appropriate amount of drug is injected, the needle 130 is distanced apart from the skin and the operation of the injector 300 is discontinued.

Accordingly, as the driving motor 312 stops, the force that presses on the rod 120 is ceased, and therefore, the pressure formed in the cylinder 110 causes the cylinder 110 and the mount 210 connected with the syringe seat and the sub-rail 212 to gravitate forward along the support block 220, thus relieving the internal pressure. Therefore, drug loss can be avoided.

According to the operation explained above, the shortcoming such as leakage of remaining drug is avoided. The foregoing exemplary embodiments and advantages are merely exemplary and are not to be construed as limiting the present invention. The present teaching can be readily applied to other types of apparatuses. Also, the description of the exemplary embodiments of the present inventive concept is intended to be illustrative, not to limit the scope of the claims, and many alternatives, modifications, and variations will be apparent to those skilled in the art.

What is claimed is:
1. A syringe device for skin treatment, comprising:
a syringe for injecting a drug into a skin through a needle at an end;
a syringe seat connected with a cylinder of the syringe receiving the drug therein to allow a reciprocation of the cylinder within a limited range according to a direction of injecting the drug;
an injector mounted on one side of the syringe seat to be rotated by a driving force to move in association with movement of the syringe seat to move a rod of the cylinder toward the needle; and a controller mounted on one side of the syringe seat and the injector to operate the injector when the needle is in contact with the skin and the syringe seat is moved to one end within a limited range, and stop the injector when the needle is apart from the skin and the syringe seat is moved to opposite end within the limited range, wherein the syringe seat is moved forward by a distance that the cylinder moves forward the needle, wherein the syringe seat comprises a mount on which the cylinder of the syringe is fixed, and a guide rail engaged with the mount at a front portion, the mount configured to receive a front end of the guide rail, and the guide rail comprises a guide groove of a predetermined length formed on a front portion, the guide groove being depressed from a top surface of the guide rail, and the mount is moveable forward and backward by a distance corresponding to the length of the guiding groove, wherein the injector comprises a driving force member operated or stopped according to the controller, to transmit a driving force to the rod, and the driving force member comprises a driving motor mounted inside the casing to rotate forward and backward, wherein, when the needle is distanced apart from the skin, the driving motor stops, and the mount and the cylinder fixed thereto together move forward along the guide groove, relieving an internal pressure of the cylinder.

2. The syringe device of claim 1, wherein the injector further comprises:

a casing comprising a space to receive the driving force member therein, and having the syringe seat mounted on a leading end thereof;

a shaft connected with the driving force member and the rod, respectively, to move in association with the driving force member to convert a rotary motion into a reciprocal motion along a lengthwise direction of the casing, thereby moving the rod toward the needle.

3. The syringe device of claim 2, wherein the driving force member further comprises:

a reducer mounted between a driving shaft of the driving motor and the shaft.

4. The syringe device of claim 2, wherein the shaft is so configured that one end is connected with an end of the driving force member to rotate forward and backward and the other end is supported on the casing and comprising a screw thread formed along an external circumference, and comprises:

a moving segment screw-coupled with the shaft to reciprocate along a lengthwise direction of the shaft, and engaged with the push rod.

* * * * *